(12) United States Patent
Andrews

(10) Patent No.: US 7,750,214 B2
(45) Date of Patent: Jul. 6, 2010

(54) PEARL MILLET LINE 53-1-1 WITH PP3 GENE AND ALL DERIVATIVES PRODUCED BY ANY METHOD

(75) Inventor: David John Andrews, Lincoln, NE (US)

(73) Assignees: Board of Regents of the University of Nebraska, Lincoln, NE (US); Chrysantis, Inc., West Chicago, IL (US)

( * ) Notice: Subject to any disclaimer, the term of this patent is extended or adjusted under 35 U.S.C. 154(b) by 98 days.

(21) Appl. No.: 12/011,049

(22) Filed: Jan. 24, 2008

(65) Prior Publication Data

US 2008/0201797 A1 Aug. 21, 2008

Related U.S. Application Data

(60) Provisional application No. 60/897,364, filed on Jan. 25, 2007.

(51) Int. Cl.
*A01H 5/10* (2006.01)
*A01H 5/00* (2006.01)
*A01H 1/00* (2006.01)

(52) U.S. Cl. ............ 800/320; 800/266; 800/298

(58) Field of Classification Search ............ None
See application file for complete search history.

(56) References Cited

U.S. PATENT DOCUMENTS

PP12,909 P2   9/2002   Skwiot 6,479,731 B1 * 11/2002 Valent et al. .......... 800/279
2003/0140382 A1   7/2003   Patell et al.

OTHER PUBLICATIONS

Azhaguvel, P., et al., "Mapping the d1 and d2 Dwarfing Genes and the Purple Foliage Color Locus P in Pearl Millet", Journal of Heredity, 2003:94(2):155-159.
Gill, B.S., "Inheritance of Pigmentation in Some Plant Parts of Pearl Millet", Indian J. Genet. Plant Breed., 1969, 29:468-472.
Hanna, W. W. et al., "Genetics of Red and Purple Plant Color in Pearl Millet", J. Hered., 1992, 83:386-388.
Kumar, K. Anand et al., "Genetics of Qualitative Traits in Pearl Millet: A Review", Crop Science, 1993, 33:1-20.
Yadav, R.P., A note on Inheritance of Pigmentation in the Coleoptilar Leaf of Pearl Millet (*Pennisetum typhoides*, S +H), Curr. Sci., 1976, 45:197.

* cited by examiner

*Primary Examiner*—Ashwin Mehta
(74) *Attorney, Agent, or Firm*—McKee, Voorhees & Sease, P.L.C.

(57) ABSTRACT

The invention relates to a pearl millet plant, seed, variety, parental line and hybrid. More specifically the invention relates to a pearl millet plant having a mutant allele that increases purple pigmentation in many plant parts. The invention relates to crossing inbreds, varieties, and hybrids containing the purple allele to produce novel types and hybrids of pearl millet and other compatible millet species, both for pigment extraction and ornamental purposes.

5 Claims, 12 Drawing Sheets
(12 of 12 Drawing Sheet(s) Filed in Color)

PEARL MILLET LINE 53-1-1 WITH PP3 GENE AND ALL DERIVATIVES PRODUCED BY ANY METHOD

CROSS-REFERENCE TO RELATED APPLICATIONS

This application claims priority under 35 U.S.C. §120 to provisional application Ser. No. 60/897,364 filed Jan. 25, 2007, herein incorporated by reference in its entirety.

BACKGROUND OF THE INVENTION

The present invention relates to a new and distinctive pearl millet line, designated 53-1-1. The term "millet" is applied to various grassy crops whose seeds are harvested for human food or animal feed. Compared to other cereal grains, millets are generally suited to less fertile soils and poorer growing conditions, such as intense heat and low rainfall and shorter growing seasons.

There are five genera of millets, Panicum, Setaria, Echinochloa, Pennisetum, and Paspalum, all of the tribe Paniceae; one genus, Eleusine, in the tribe Chlorideae; and one genus, Eragrostis, in the tribe Festuceae. The most important cultivated species of millet are foxtail (Setaria italica), pearl or cattail millet (Pennisetum glaucum), proso (Panicum miliaceum), Japanese barnyard millet (Echinochola crusgalli), finger millet (Eleusine coracana), browntop millet (Panicum ramosum), koda or ditch millet (Paspalum scrobiculatum), and teff millet (Eragrostis tef).

The present invention relates to Pennisetum glaucum (L) R&BR, commonly known as pearl millet. Pearl millet, a cross-pollinating diploid (2n=14), is one of about 140 Pennisetum species worldwide which differ in both chromosome number (5, 7, 8 or 9) and ploidy level. The pearl millet gene pool is limited to cultivated pearl millet—Pennisetum glaucum ssp glaucum; polymorphic wild pearl millet—Pennisetum glaucum ssp monodii (from which cultivated varieties were domesticated), and the resultant weedy intermediate populations—Pennisetum glaucum ssp stenostachyum. Pearl millet will also cross naturally with elephant grass, Pennisetum purpureum (Schum.), a tetraploid (2n=28), but the resulting hybrids being triploid are sterile. Pearl millet will not naturally hybridize with other millet species but hybrids have been made artificially with several Pennisetum species, however these have all been reproductively defective.

Pearl millet originated in sub-saharan west Africa and is principally grown as a food grain in Africa and southeast Asia, mainly India, with crop residues used as forage, fuel and construction. It is also grown principally for forage in Brazil, the USA and Australia and dwarf grain hybrids have potential as feed grain for poultry. West African land race cultivars range from 35 to 140 days to flowering and from 1.5 to 5.0 m tall. 1 to 5 basal tillers bear dense cylindrical spikes from 20 cm to 2 m long. Globose to cylindrical grains are 2 to 4 mm long and weigh 5 to 20 g./1000. Short duration cultivars can successfully mature in warm temperate summers as far as 50_ from the equator provided there sufficient days above 10_C. (60_F). Pearl millet is not frost tolerant.

Pearl millet cultivars are either varieties (stable heterozygous intermating populations) or F1 hybrids usually made from inbred parental lines. New varieties are usually produced by population breeding (for example recurrent selection), and parental lines by pedigree (for example head to row) breeding.

Single cross hybrids (F1 plants resulting from crossing two inbred lines) represent the most practical genotype to consistently deliver productivity and quality. Such hybrids have utility in pearl millet. The breeding of parental lines that which, in combination will contribute productivity and specific desired qualities to a hybrid is a lengthy breeding process. This requires the generation of appropriate genetic variability from which inbred lines with new recombinations of desired traits can be obtained through selection procedures and combining ability tests. Separate breeding streams are required for male and female parents.

Pearl millet is a wind cross pollinated diploid species where all flowers on a head are perfect (most flowers contain functional male and female parts). Thus, to produce 100% hybrid seed, one parental line should be male sterile (female fertile only) which will ensure that all seed set on that line will be hybrid seed resulting from pollination by the other normally male fertile parent (provided other pollen sources are excluded). In pearl millet the production of all male sterile plants in quantity is achieved by the use of a cytoplasmic—nuclear male sterility (CMS) system, of which there are several, the most useful being $A_1$ (the original), $A_4$ and $A_5$.

To repeatedly reproduce seed of a CMS male sterile line involves the use of the same nuclear genome in two different cytoplasm types (cytoplasm is normally only maternally inherited, and carries non-nuclear genes which rarely change). The cytoplasm type where a line is normally both male and female fertile is designated "normal". When pollen from this line, which carries haploid set of nuclear genes, but (normally) no cytoplasm, pollinates a plant which is CMS male sterile (and therefore is said to have "sterile"[inducing] cytoplasm) but female fertile, the progeny from this cross may be of several types in regard to male fertility (fertile pollen):

a) All male sterile.
b) all partially male fertile.
c) segregate for plants that are completely male fertile, or completely male sterile.
d) All fully male fertile.
e) A mix of some or all the above.

When the progeny are all male sterile, (case a) the pollen donor line is classified as a maintainer line (designated a B-line by convention), in respect of that particular CMS system, since it maintained the state of male sterility. This line can be used to make an iso-nuclear male sterile seed parent (below).

If on the other hand, the progeny are all male fertile, (case d) then the pollen donor line is said to be a restorer (by convention an R-line) in respect of that CMS system, since it restored male fertility. Restorer lines can be used directly as male parents to make hybrids in that CMS system. R lines carry nuclear genes for male fertility that tend to be dominant and are usually specific to a CMS system. One line can be R in respect of one system and B in another.

Cases b) and e) show the pollen donor line has little utility to become a hybrid parent on that CMS system. Case c) indicates that the pollen donor line is still segregating for these factors and either a B or an R line could be produced by further selection and test crossing.

By repeated back crossing using pollen from the B-line starting with the male sterile $F_1$ (case a), the nuclear genome of the B line can effectively replace the nuclear genome of the line donating the (male) sterile inducing cytoplasm. The resulting male sterile line, which is then of the same nuclear constitution of the B line but in sterile cytoplasm, is by convention called an A line, also known as a seed parent. More A line seed can be increased by pollination with the B line. Pure seed of a hybrid which will be male fertile can then be produced in quantity by pollinating sufficient A line plants with R line pollen in isolation from other sources of pollen. Or, if it is desirable, a male sterile hybrid can be produced by crossing an A-line with a non-restoring line (in effect another B line) of a different and complementary nuclear constitution.

Red or purple plant pigmentation, due to the presence of anthocyanins, occurs naturally in pearl millet germplasm, either on specific plant parts or more generally over the plant. In the latter case, young plants appear normal green until 20-30 days old (the juvenile growth phase) when pigmentation on leaf blades becomes progressively more evident. However, on all seedlings of prior cultivars that later have general red or purple coloration, traces of this coloration develop as early as five days after emergence on leaf margins but not before 10 days on the keel of the first leaf midrib.

SUMMARY OF THE INVENTION

The present invention relates to a novel millet line (or cultivar) designated 53-1-1 that was selected from a single unique plant. 53-1-1 plants are of moderate height (1.3 m), low tillering with strong stalks and 18 to 22 long broad leaves, turning dark purple before flowering. The Inventor believes that he is the first to identify a pearl millet where purple pigment formation begins in the developing tissues of leaves, stem internodes and heads before their emergence, demonstrating the initiation of pigment formation in this case is not photo-dependant. The Inventor further believes that he is the first to discover that the same pearl millet exhibits other unique traits, for example, (i) the presence of a thin dark purple line on the keel of the midrib of the first seedling leaf before 10 days old, (ii) a more intense darker purple color on fully developed leaves stems and heads than other colored purple millets, (iii) the under side of mature leaf blades is as darkly pigmented or darker than the upper side of the leaf of a 53-1-1 plant and (iv) the presence of extensive purple color in the interior (core) of stems after grain maturity.

The 53-1-1 line also has a novel gene, designated Purple Plant 3 (PP3), which results in the purple pigmentation that develops in the leaf, stem, head and grain. Although the initial formation of pigment is not light induced, subsequent exposure to light further increases production to higher levels of intensity not found in other pearl millets. See Table 2 and FIGS. 1-3.

This invention thus relates to the seeds of millet line 53-1-1, to the plants of millet line 53-1-1 and to methods for producing a millet plant by crossing of the line 53-1-1 with itself or with another millet line or cereal line, for example, maize, sorghum, wheat, barley, oat or rice plants. The invention further relates to seeds of line 53-1-1 further comprising the PP3 gene. The invention also relates to plants of line 53-1-1 further comprising the PP3 gene. The invention includes methods for producing a millet plant by crossing the millet plant of cultivar 53-1-1 further comprising the PP3 gene with itself or with another millet genotype.

This invention further relates to the descendants of all progeny resulting from crosses with 53-1-1 including derivatives of subsequent generations of crosses identifiable by the unique association of purple color traits described above and in Table 2 and demonstrated to be visibly different in relation to other documented sources of red/purple color as shown in the photographs of FIGS. 1 to 23. This invention relates to any use of seeds or plants of any kind derived from plants showing this unique association of purple traits. All plants, whether pearl millet, elephant grass or other species produced by using pearl millet line 53-1-1 or its descendants, or which incorporate the PP3 gene whether produced by conventional or artificial gene transfer techniques, are within the scope of this invention.

Thus, in one aspect, the invention includes the pearl millet cultivar of 53-1-1, a millet plant, or a part thereof, including pollen, an ovule or a seed. In another aspect, the invention concerns a method of producing a millet seed that includes crossing a first parent millet plant with a second parent millet plant and harvesting the resultant hybrid millet seed. In a particular embodiment, the first or second parent pearl millet plant is the cultivar known as 53-1-1.

In another aspect, the invention concerns a method of developing cereal plants with red/purple pigmentation that is not initially photo-dependent that includes introducing the PP3 gene into the plant. In another aspect, the method includes backcrossing the PP3 gene into the plant. In another aspect, the invention includes a cereal plant or a seed of the cereal plant produced by this method or any other suitable method. The invention also provides for a 53-1-1 variety of pearl millet as characterized in one aspect by a thin line of purple pigmentation on the keel of a midrib of a first seedling leaf 7 to 10 days after emergence.

In a further aspect, the invention concerns a cereal plant having purple pigmentation that is a result of a PP3 gene having been introduced to the plant. In one aspect, the cereal plant is a millet plant. In another aspect, the cereal plant is a maize, sorghum, wheat, barley, oat or rice plant. In yet a further aspect, the invention concerns a PP3 gene.

In another aspect, the present invention provides for a cereal plant or its progeny that has red/purple pigmentation that is not initially photo-dependent. In one aspect, the cereal plant is a millet plant. In another aspect, the cereal plant is a pearl millet plant. In another aspect, the plant has red/purple pigmentation on the underside of leaves that is as dark or darker than the upper side of the leaves, on the peduncle, and/or internode parts covered by leaf sheath and inside the stem after grain maturity.

In a still further aspect, the invention concerns a method for producing a seed comprising crossing a first parent plant which includes a PP3 gene and exhibits the PP3 pigmentation with a second parent plant and harvesting the resultant hybrid seed. In one aspect, the first or second plant is a millet plant. In another aspect, the first or second plant is a pearl millet plant. In another aspect, the first or second plant is a cereal plant. In another aspect, the first or second plant is an Elephant grass plant.

In another aspect, the invention provides a method for producing anthocyanins that includes recovering anthocyanins from a 53-1-1 plant or part thereof or a plant that includes the PP3 gene. In another aspect, the method further includes growing the 53-1-1 plant or part thereof or a plant that includes the PP3 gene. In another aspect, the method further includes harvesting the 53-1-1 plant or part thereof or a plant that includes the PP3 gene. In another aspect, the method further includes extracting or purifying the anthocyanins.

DESCRIPTION OF THE FIGURES

The patent or application file contains at least one drawing executed in color. Copies of this patent or patent application publication with color drawing(s) will be provided by the Office upon request and payment of the necessary fee.

The figures illustrate the differences, at various growth stages, between plants carrying the PP3 gene (FIGS. 1-3), and plants from several examples of the prior art in red/purple coloration in pearl millet (FIGS. 1-16). The examples of prior art are: Purple Majesty, a widely grown ornamental F1 hybrid; NM9, the inbred female parent of Purple Majesty; IP 18293 (containing the PP gene) and IP 8166, both from the Pearl Millet World Collection held at ICRISAT, India; Tift 89-18 (containing the Rp2 gene) and Tift 89-19 (Rp1 gene), both from USDA Tifton GA.

FIG. 6 shows mature leaves and heads.

FIG. 17 compares leaves of same age and position from NM9, the female inbred parent of Purple Majesty and inbred line 53-1-1. Left to right; female parent of Purple Majesty, lower and upper leaf surfaces: Line 53-1-1, lower and upper leaf surfaces. Note lower surface of 53-1-1 leaf is darker than upper side.

FIG. 18 shows a comparison of a seedling of Purple Majesty (Pm) with a PP3 seedling at the 7 day old first leaf stage. No color is evident on the midrib keel of the first leaf of Purple Majesty, while that of PP3 has a colored line.

FIG. 19 shows 7 day old seedlings of two lines with the virescent (yellow) chlorophyll trait into which both the color of Purple Majesty (Pm) and PP3 have been separately crossed. The first leaf of the Purple Majesty type shows no line while that with PP3 does.

FIGS. 20 and 21 show adult clones of F1 crosses with *Pennisetum* purpureum (Elephant Grass) with female of Purple Majesty and PP3. In FIG. 20 the Purple Majesty female parent crossed with elephant grass results in a clone with medium purple foliage with green young leaves and whorls. In FIG. 21 the plants of the clone with PP3 have no green whorls and are all dark purple.

FIG. 22 shows comparison of the split stems of two comparable inbreds, one with and one without PP3. On the left is line 53-1-1(PP3) the interior of which is strongly purple, and (right) the female parent of Purple Majesty (Pm) the interior of which is pale.

FIG. 23 shows the cut stems of clones of crosses of PP3 and Pm with Elephant grass. The cross with Elephant grass and female of Purple Majesty (Pm) shows faint color, while the cross with PP3 exhibits an intense purple color.

DEFINITIONS

In the description and tables that follow, a number of terms are used. In order to provide a clear and consistent understanding of the specification and claims, including the scope to be given such terms, the following definitions are provided:

Maturity Date. Plants are considered mature when 95% of seeds on first head have hardened.

Plant Height. Plant height is taken from the top of soil to top of the plant and is measured in centimeters.

Grain Yield. Grain yield is measured in pounds per acre of harvested seed.

Grain Length (L). Length of a millet grain is measured in millimeters.

1000 Grain Wt. The weight of 1000 millet grains as measured in grams.

A plant having essentially all the physiological and morphological characteristics means a plant having the physiological and morphological characteristics, except for the characteristics derived from the converted gene.

Plant Part. Includes plant protoplasts, plant cell tissue cultures from which millet plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like.

Regeneration refers to the development of a plant from tissue culture.

DETAILED DESCRIPTION OF THE INVENTION

Pearl millet line 53-1-1 is a semi dwarf, late maturing, wide leafed line which exhibits traits conferred by the PP3 gene, including a distinct, intense purple color that develops in its leaf, stem, heads and grain. The initial induction of the purple pigment on covered plant parts prior the juvenile growth phase is not photo-dependent, although it is further intensified on exposed plant parts by light. This is in contrast to other purple pearl millet plants that have been identified to date.

Figure 2:
FIGS. 1, 2 and 3 show the coloring of PP3, the genetic sequence of the invention. The leaf whorls are all colored with no green (FIG. 1). The base of emerging heads is not green but already light purple (FIG. 2). The foliage is darker than that of Purple Majesty, the undersides of the leaves are dark, and the peduncles under the leaf sheath are purple (FIG. 3). (See also FIG. 17 for comparisons of upper and underside leaf colors).
Figure 1:
Figure 18:
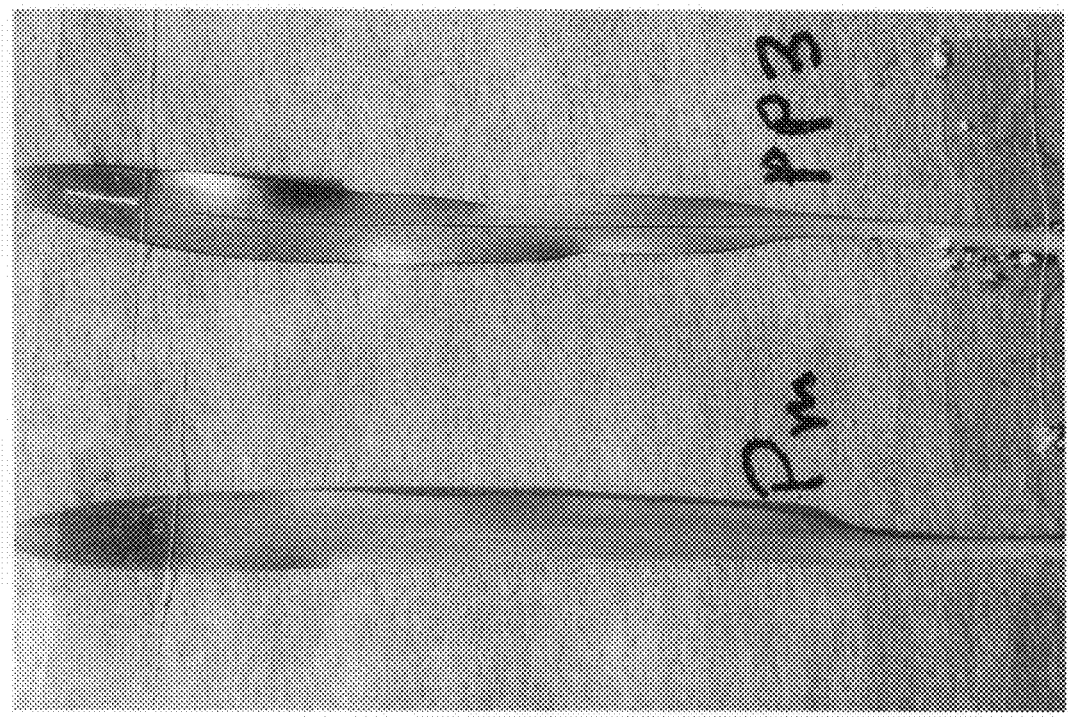
FIGS. 18 and 19 compare the seedling marker (dark line on keel of first leaf midrib) present in PP3 plants and absent in prior art seedlings.
Figure 17:
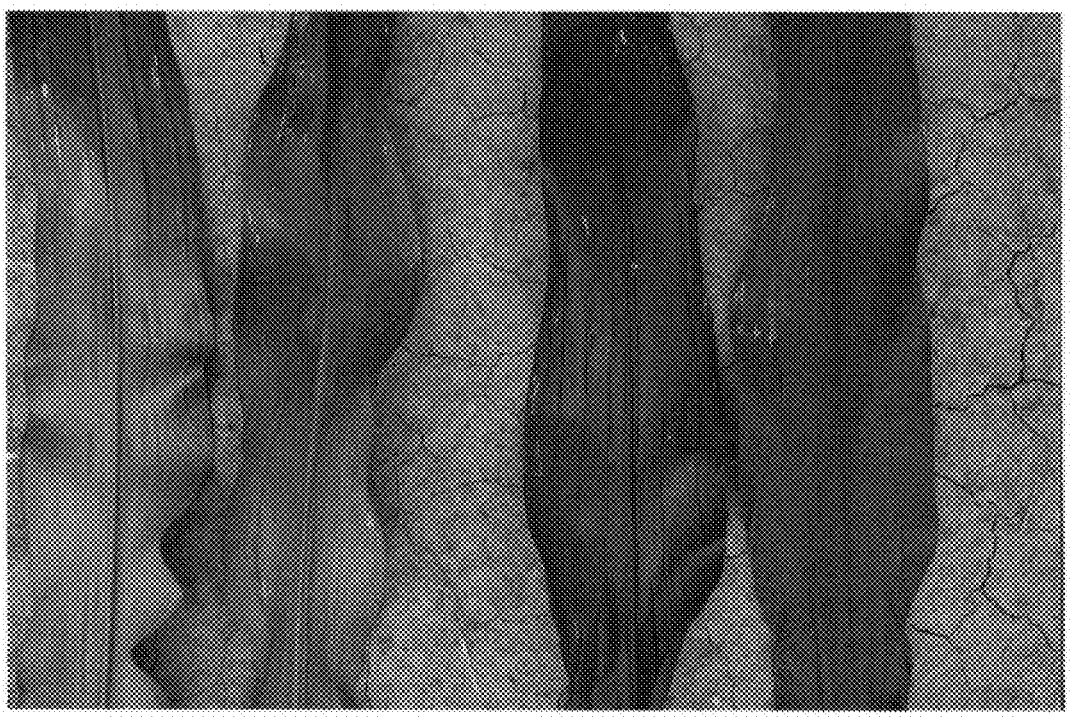
FIGS. 17 and 22 compare upper and lower leaf coloration and stem core color of inbred line 53-1-1 with the prior art in inbred line NM9.
Figure 20:
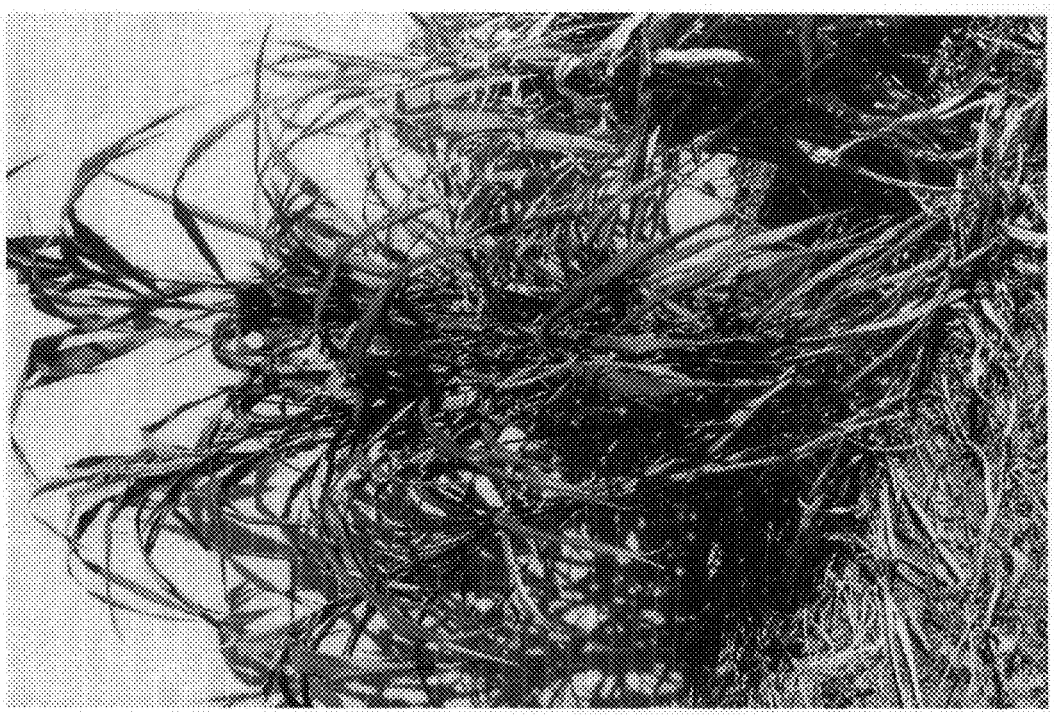
FIGS. 20, 21 and 23 show the effect of the PP3 gene compared to the prior art in F1 crosses with Elephant Grass.
Figure 19:
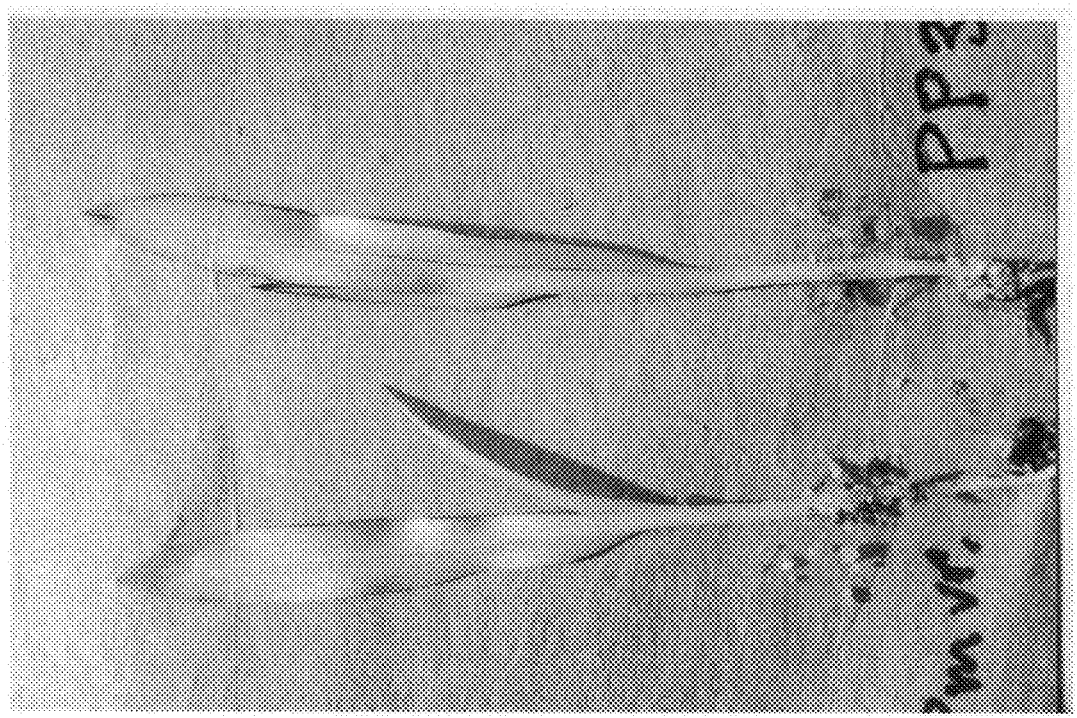
Figure 21:
Figure 22:
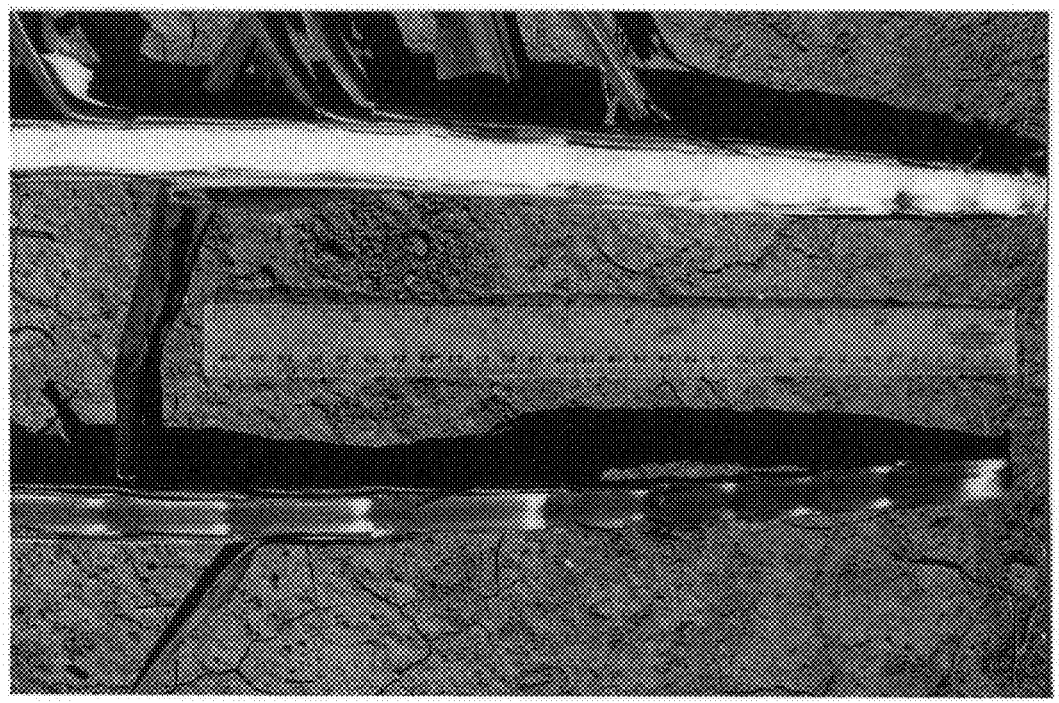

Crosses of line 53-1-1 with characterized color stocks known to produce red or purple plant color showed that the intensity and distribution of the color produced by 53-1-1 was categorically different and dominant to all other available color sources. The intensity and phenotypic expression of the color produced in F1 crosses and the segregation of this expression in each of the F2 cross populations indicated that PP3 acts as a single dominant gene. The specific effects of PP3 are a thin dark purple colored line on the keel of the midrib of the first seedling leaf 7 to 10 days after emergence (FIGS. 18-19), the emerging leaves in whorls of adult plants (FIG. 1) are colored, Royal Horticulture society (RHS) color card 173C (see reference Royal Horticulture society, London, UK, 1995). The adult leaves are dark purple on both the top (RHS color card 187A) and the underside (RHS color card 187-200A). See FIGS. 2 and 17. Leaf sheaths and all floral parts except anthers are purple (FIG. 2). The interior stems after grain maturity are purple RHS color card 187B (FIG. 22).

Figure 4:
FIGS. 4, 5 and 6 show the coloring of Purple Majesty, a commonly grown cultivar typical of the prior art color in pearl millet. The cultivar shows emerging leaves forming green whorls (FIG. 4), the emerging head has a green sector (that emerged the previous night) (FIG. 5)
Figure 3:
Figure 6:
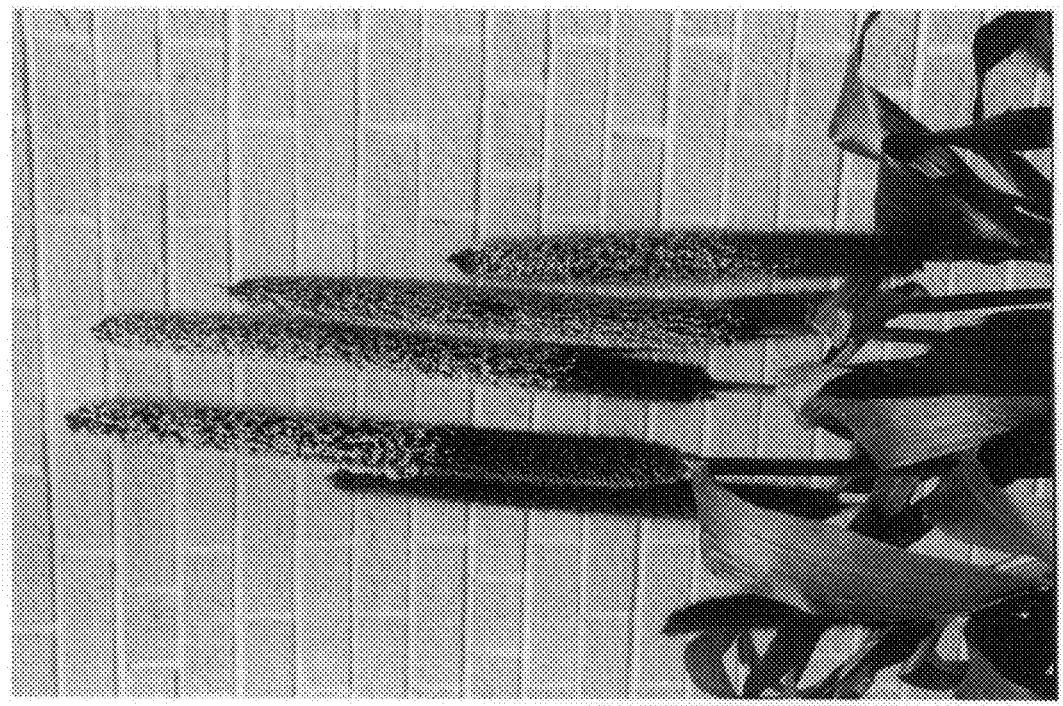
Figure 5:
Figure 8:
FIGS. 7 and 8 show the coloring of IP18293, another example of the normal existing purple color. The whorls are green (FIG. 7) and the peduncles under the removed leaf sheath are green (FIG. 8). The leaves also show a significant amount of green (FIG. 8).
Figure 7:
Figure 10:
FIGS. 9, 10 and 11 show the coloring of Tift 89-18 (purple source). The laminas are green with dark midribs (FIG. 9), the base of emerging heads are pale (FIG. 10) and the peduncles are pale (FIG. 11) (the center peduncle is exposed by opening the leaf sheath).
Figure 9:
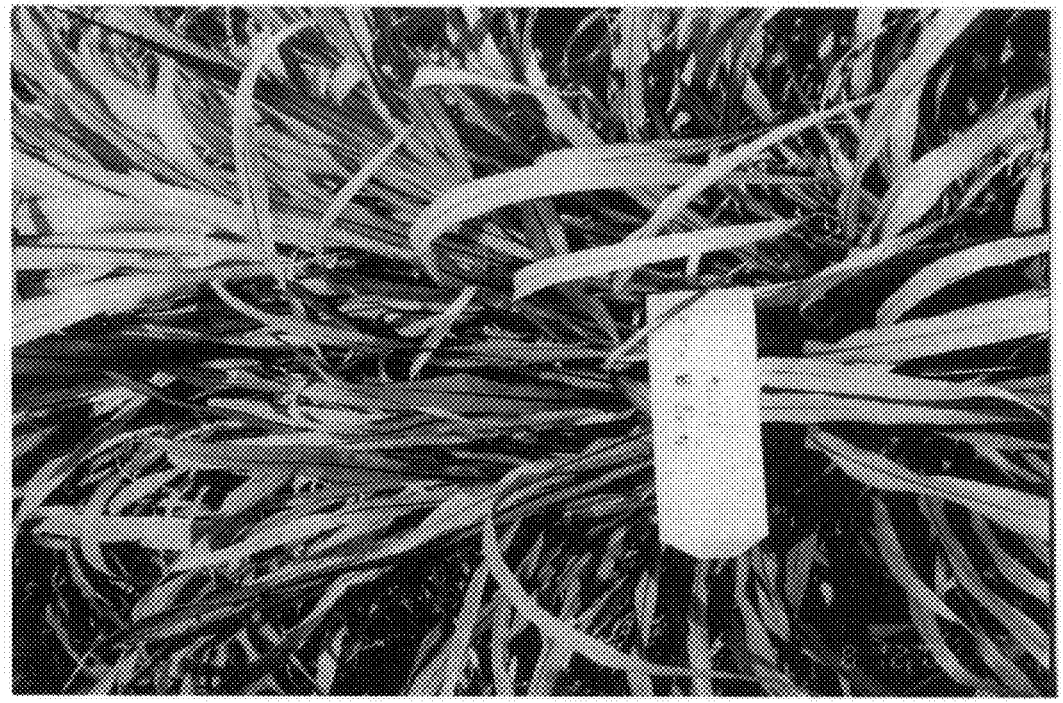
Figure 12:
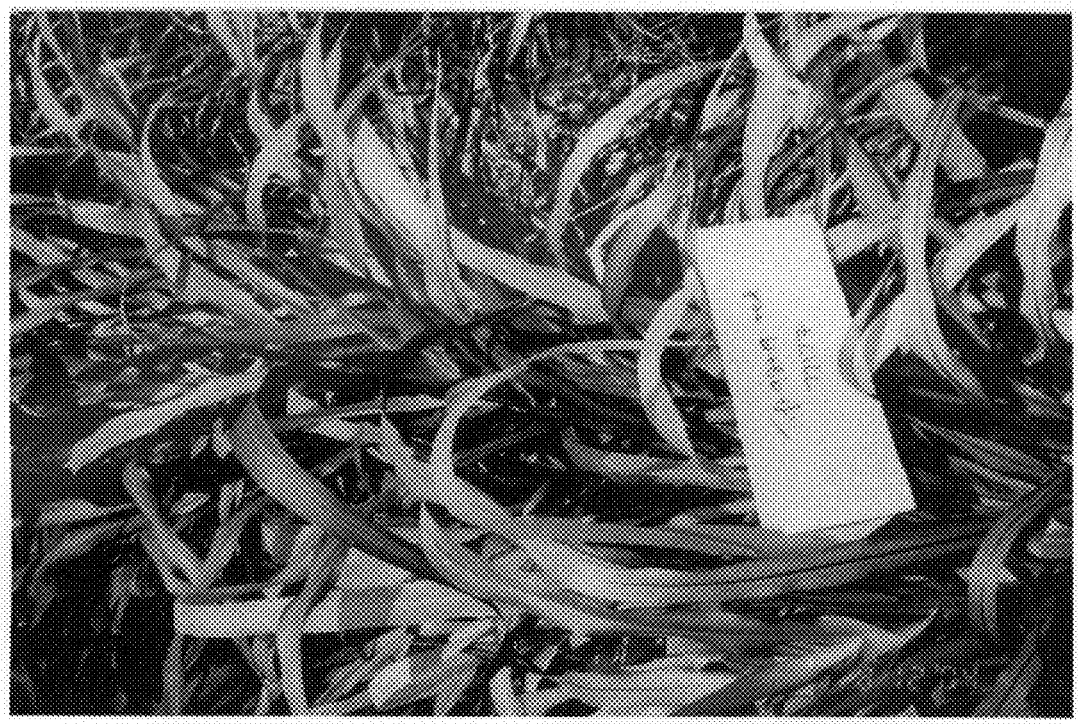
FIGS. 12, 13 and 14 show the coloring of Tift 89-19 (red source). The plants have green whorls with reddish laminas (FIG. 12). The base of emerging heads is green (FIG. 13) and the peduncle is pale (FIG. 14). (The center peduncle is exposed).
Figure 11:
Figure 14:
Figure 13:
Figure 16:
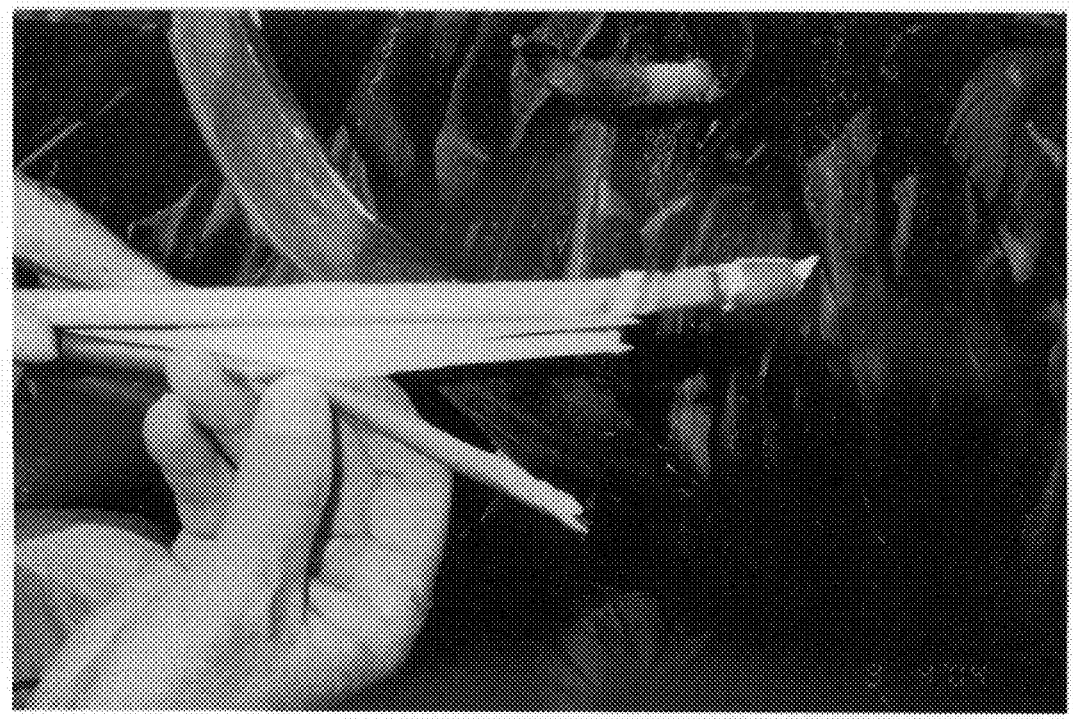
FIGS. 15 and 16 show coloring of IP8166, a further example of existing purple color. Again the base of the emerging head is green (FIG. 15) and the exposed peduncle is pale (FIG. 16). Also evident is the green sector on the head emerging in the later developed tiller (FIG. 16).
Figure 15:

Red/purple plant color in prior purple millets develops in emerging adult leaves in response to light. Thus, on prior millets the parts of leaves or heads which emerge at night, remain green for some hours after sunrise, leading to green whorls where leaves emerge and green bands at the bottom of emerging heads (see examples in FIGS. 4 and 5). The underside of leaves is essentially green. Other covered parts, such as stem internodes under leaf sheaths, are not pigmented or very pale where the covering is thin. On the contrary, in adult plants carrying the PP3 gene, the emerging leaves (FIG. 1) heads have no light band (FIG. 2) and are distinctly colored before emergence and darken further during daylight to an intensity that clearly exceeds the level of color expression of all other purple sources.

The PP3 trait has been made homozygous in this elite germplasm to create a stable line with this novel gene. The purple trait is dominant and thus confers this color whether in a homozygous or heterozygous state. It has been self-pollinated a sufficient number of generations. The line has been increased with continued observation for uniformity. Millet Cultivar 53-1-1 has the following morphologic and other characteristics (based primarily on data collected at Lincoln, Neb.).

ing a millet cultivar 53-1-1-derived millet plant by crossing the pearl millet cultivar 53-1-1 with a second millet plant and growing the progeny seed, and repeating the crossing and growing steps with the millet cultivar 53-1-1-derived plant from 0 to 7 times. Therefore, any methods using the cultivar 53-1-1 or with the PP3 gene are part of this invention, including selfing, backcrosses, hybrid breeding, and crosses to populations. Any plants produced using cultivar 53-1-1 or any plant with the PP3 gene as a parent are within the scope of this invention. Thus, another aspect of this invention is to provide for cells which upon growth and differentiation produce a cultivar having essentially all of the physiological and morphological characteristics of 53-1-1. As used herein the term "PP3 gene" or "new PP3 gene" or "PP3 trait" shall mean a nucleotide sequence present in 53-1-1 in homozygous form and which results in plants exhibiting the pigmentation characteristics described herein. The PP3 gene may be a mutation of an existing gene, a new gene derived from recombination, a suppressor or enhancer sequence or any other genetic anomaly responsible for the novel red/purple pigmentation described herein.

Advantageously, the 53-1-1 pearl millet cultivar may be used in crosses with other, different, millet cultivars or cereal plants to produce first generation (F1) millet seeds and plants with superior purple pigmentation characterized by the a thin line of purple pigmentation on a the keel of a midrib of a first

TABLE 1

Variety Description Information

| | | |
|---|---|---|
| Days to maturity: | | 105 days |
| Culm: | | 110 cm tall |
| Leaf color at flowering: | upper surface | dark purple RHS color card 187 A |
| | under surface | purple/black RHS color card 187 A/200 A |
| Leaf Blades: | | 63 cm long × 7.5 cm wide ($4^{th}$ leaf below flag leaf) |
| Leaf Sheaths: | | 13 cm long × 1.3 cm wide (covers node above by ⅓ - $4^{th}$ leaf below flag leaf) |
| Leaf hairs: | | 1.5 mm long, dense on upper and lower surface of leaf and outer surface of leaf sheath. |
| Leaf hair color: | | Black/purple, hair color develops earlier than color in lamina |
| Panicles: | | 18 cm long × 2 cm wide |
| Peduncle diameter: | | 6 mm |
| Involucres: | | 2 fertile florets per involucre (average mid panicle) |
| Involucre bristles: | | numerous, 3-4 mm long, (not protruding beyond panicle surface) |
| Spikelets: | | 4 mm long |
| Upper Glume: | | 2 mm |
| Lower Glume: | | 1 mm |
| Lemma: | | 3 mm |
| Palea: | | 3 mm |
| Grain: | | Length 2.5 mm, width 2.0 mm |
| Grain Shape: | | obovate, slightly pointed at base |
| Grain Color: | | Dark Purple, hilum black/purple |
| Grain weight: | | 4.5 g./1000 |
| Grain productivity: | | 800 lb/ac. (890 kg/ha.) |
| Plant height and productivity: | | variable, depending on management and available moisture |

This invention is also directed to methods for producing a millet plant by crossing a first parent millet plant with a second parent millet plant, wherein the first or second millet plant is the pearl millet plant from the line 53-1-1 or a millet plant which incorporates the PP3 gene. Further, both first and second parent millet plants may be from the cultivar 53-1-1 or have the PP3 gene. Further, both first and second parent millet plants can come from the pearl millet cultivar 53-1-1. Still further, this invention also is directed to methods for producseedling leaf 7 to 10 days after emergence, color on emerging leaves, dark purple on both a top and an underside of adult leaves, leaf sheaths, all floral parts except anthers and at maturity stem interiors are purple.

The utility of the pearl millet cultivar 53-1-1 also extends to crosses with other species. Common species used include: *Panicum, Setaria, Echinochloa, Pennisetum,* and *Paspalum,* all of the tribe Paniceae; one genus, *Eleusine,* in the tribe Chlorideae; and one genus, *Eragrostis,* in the tribe Festuceae.

The most important cultivated species of millet are pearl or cattail millet (*Pennisetum glaucum*), foxtail (*Setaria italica*), proso (*Panicum miliaceum*), Japanese barnyard millet (*Echinochola crusgalli*), finger millet (*Eleusine coracana*), browntop millet (*Panicum ramosum*), koda or ditch millet (*Paspalum scrobiculatum*), and teff millet (*Eragrostis tef*).

Culture for expressing desired structural genes and cultured cells are known in the art. Also, as known in the art, the millet is transformable and regenerable such that whole plants containing and expressing desired genes under regulator control may be obtained.

The invention also relates to the PP3 phenotype and its underlying genetic basis. According to the invention, 53-1-1 can be used as a breeding source for this gene to incorporate the purple color into other cereal varieties or lines. The variety may also be used to isolate proteins encoded by the PP3 gene, or nucleotide sequences and variants for the same. Further, it is contemplated that proteins associated with the trait of purple pigmentation may also be elucidated using standard techniques known to those in the art. This invention also is directed to methods for producing a pearl millet plant by crossing a first parent plant with a second parent plant wherein either the first or second parent plant is the variety 53-1-1 or a plant which preferably incorporates the PP3 gene derived from this plant. Further, both first and second parent plants can come from 53-1-1. Still further, this invention also is directed to methods for producing a 53-1-1-derived millet plant by crossing variety 53-1-1 with a second millet plant and growing the progeny seed, and repeating the crossing and growing steps with 53-1-1-derived plant from 0 to 7 times. Thus, any such methods using 53-1-1 are part of this invention: selfing, backcrosses, hybrid production, crosses to populations, and the like. All plants produced using 53-1-1 as a parent are within the scope of this invention including plants derived from 53-1-1. The variety may also be used as a source of the PP3 gene to generate purple plants by breeding with the same. This can be done in even a single backcross generation as the purple color is dominant and is expressed with only a single copy of the gene. This can be done in a single and/or successive backcross generations. Thus, the invention includes any plant expressing the PP3 gene in the variety which may also be used to isolate the proteins involved and responsible for the purple color including any genes associated therewith. Advantageously, the inbred line may be used in crosses with other, different, inbreds to produce first generation (F1) hybrid seeds and plants with superior characteristics, such as those described herein.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native or endogenous genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed cultivar.

Methods for transformation of pearl millet are disclosed in U.S. patent application Ser. No. 10/204,851 (Publication No. 2003/0140382 by Patell et al, published Jul. 24, 2003 entitled "Process for generating genetically modified pearl millet through *agrobacterium* and biolistic transformation".) Such transgenic techniques can be used for a variety of modifications as is known in the art, such as herbicide and plant disease resistance genes, see, for example, J. J. Goldman et al., *Plant Cell Reports* 21(10):999-1009 (2003) (describing herbicide-resistant transgenic pearl millet plants produced by microprojectile bombardment of embryogenic tissues with the bar gene.); A. Madhavi Latha et al., *Plant Cell Reports* 25(9):927-935 (2006) (developing of transgenic pearl millet (*Pennisetum glaucum* (L.) R. Br.) plants resistant to downy mildew); Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*). A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt-endotoxin gene. Moreover, DNA molecules encoding-endotoxin genes can be purchased from American Type Culture Collection (Rockville, Md.), for example, under ATCC Accession Nos. 40098, 67136, 31995 and 31998. An enzyme inhibitor, for example, a protease inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), and Sumitani et al., *Biosci. Biotech. Biochem.* 57:1243 (1993) (nucleotide sequence of *Streptomyces nitrosporeus*-amylase inhibitor), an insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone, an insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins. an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene, a molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

Other examples include, genes that confer resistance to a herbicide. For example: glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Application No. 0 242 246 to Leemans et al. De Greef et al., *Bio/Technology* 7:61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83:435 (1992).

Yet another example is a gene that confers or contributes to a value-added trait, including but not limited to modified fatty acid metabolism, for example, by transforming a plant with an antisense gene of stearoyl-ACP desaturase to increase stearic acid content of the plant. See Knultzon et al., *Proc. Natl. Acad. Sci. USA* 89:2624 (1992). Other value added changes include decreased phytate content. Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. Yet another example is modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus* mutants fructosyltransferase gene), Steinmetz et al., *Mol. Gen. Genet.* 200:220 (1985) (nucleotide sequence of *Bacillus subtilis* levansucrase gene), Pen et al., *Bio/Technology* 10:292 (1992) (production of transgenic plants that express *Bacillus licheniformis*-amylase), Elliot et al., *Plant Molec. Biol.* 21:515 (1993) (nucleotide sequences of tomato invertase genes), Sagaard et al., *J. Biol. Chem.* 268:22480 (1993) (site-directed mutagenesis of barley-*amylase* gene), and Fisher et al., *Plant Physiol.* 102:1045 (1993) (maize endosperm starch branching enzyme II).

The plants of the present invention may be grown for ornamental, horticultural appeal, similar to the Purple Majesty millet hybrid that received the All-America Selections Gold Medal winner for 2003. Breeding the 53-1-1 plant or incorporating the PP3 gene into other plants is an effective method of producing a new variety of other purple, non-photo-dependent, pigmented plants. The most important of the purple pigment molecules are the naturally occurring compound anthocyanins, particularly pelargonidins, cyanidins and delphinidins. The functions of these pigments extend well beyond coloration of the plant. For example, it is known that plant anthocyanins may be used as nutraceuticals, dyes or colorants. Thus, the pearl millet plant or any plant containing the PP3 gene, for example, a transgenic plant, of the present invention may be a source of anthocyanins suitable for, but not limited to, uses described herein.

Thus, in one aspect of the invention, anthocyanins obtained from the 53-1-1 pearl millet plant or any plant derived from it containing the PP3 gene may be used as a nutraceutical or as ingredients in a pharmaceutical composition. For example, anthocyanins may be used for the preservation of oxidation sensitive compositions or included in pharmaceutical compositions in a manner known per se for anthocyanins from other sources, as e.g. described in WO 92/03146. Such pharmaceutical compositions may be used in the treatment of wounds, ulcers, inflammatory symptoms, and pathogenic conditions of the vascular system or of disturbances caused by a deterioration of the lipoid or glycide metabolisms. In addition, compositions comprising the anthocyanins of the invention may be used to improve (night) vision and/or treat tired eyes. Such compositions may further be used in the prevention of cancer and cardiovascular disease, and in reducing the effects of ageing, such as impaired memory. In addition, anthocyanins obtained from plants of the invention may be used to treat conditions or diseases that would benefit from the reduction of oxygen radicals such as superoxide anion radical, hydrogen peroxide, hydroxyl radical, alkoxyl radicals, peroxyl radicals for singulett oxygen, and many other radicals since anthocyanins are known radical scavengers. As such, anthocyanins may be used to aid the prevention of cancer or may delay the effects of ageing. Advantageously, since the plants of the invention have been obtained through classical breeding techniques rather than genetically modified, the public may have greater acceptance of these plants or products therefrom.

This makes the plants favorable for use in other consumable products, including but not limited to naturally-occurring pigments for use as dyes or food coloring. The anthocyanins may be a natural alternative to synthetic coloring agents, which in the past have had their safety questioned by the Food and Drug Administration, for example, red dyes No. 2 and No. 4. Anthocyanin pigments are biodegradable, water soluble, and pH sensitive; they are not suspected toxins or carcinogens. In fact, Miniati and Coli have reported that ingested anthocyanins can lower cholesterol, inhibit platelet aggregation, and exhibit anti-thrombotic and antioxidant properties. (Miniati, E. and Coli, R., "Anthocyanins: Not only Color for Foods," *The First International Symposium on Natural Colorants*, Francis, Dr. F. J., Ed. (1993) available through the Herald Organization, Hamden, Conn.). Thus, anthocyanins are suitable for human and/or animal consumption for a variety of purposes. As described in U.S. Pat. No. 5,908,650, anthocyanins can be made stable for use in coloring foods and beverages. In addition to food or food additives, anthocyanins of the present invention may be used as dyes for coloring plant fibers, for example, in clothing and baskets.

The 53-1-1 pearl millet plant or any plant derived from it containing the PP3 gene is believed to be a rich source for anthocyanins. Thus, in a further aspect, the invention relates to methods for producing anthocyanins. The method includes recovering the anthocyanins in a 53-1-1 pearl millet plant or any plant derived from it containing the PP3 gene and optionally purifying or extracting the anthocyanins using any suitable techniques. Another aspect of this method includes growing a plant of the invention and harvesting the plant or a part thereof. The plant suitable for use in the methods of the present invention may be any of the plants as described herein. Recovery of the anthocyanin may include grinding or homogenization of the plant and may further include extraction of the anthocyanins. Methods for recovery and extraction of anthocyanins from plant materials are well known in the art and may likewise be applied to the plants of the invention. In another aspect, the anthocyanins may be purified, for example, using chromatography (see Fiorini, 1995, *J. Chromatogr,* 692:213-219). Anthocyanins have been extracted from plants and fruits by various procedures using for example, sulfur dioxide, Shrikhande, in U.S. Pat. No. 4,452, 822, or bisulfite, Gabetta, et al., in U.S. Pat. No. 5,200,186, with anhydrous methanol, Lietti, in U.S. Pat. No. 4,413,004. The above examples describe some processes known in the art for extracting and isolating anthocyanins from various plant materials. The anthocyanin obtained from the 53-1-1 pearl millet plant or any plant derived from it containing the PP3 gene employing the described methods or any other suitable method may be used in a variety of products. As described above, anthocyanins obtained from plants of the invention may be included in products for consumption, including, for example, nutraceuticals, pharmaceutical compositions, foods or drinks.

EXAMPLES

Example 1

A previously unknown high level of purple plant coloration with a wider distribution of purple color within the plant was discovered in one plant in a research field in 2002. The plant was in one family of nine similar purple plant F8 families selected from the cross NM9B×IP 18293. NM9B was derived from a cross between two F1's each of which resulted from crosses between IP18293 and different experimental lines. IP18293 is a characterized dwarf purple germplasm stock from the pearl millet World Collection held at ICRISAT, Hyderabad, India.

The very dark purple phenotype of the present invention segregates as a simple dominant allele.

Each F1 of crosses made directly with pollen from the discovered plant to 10 different normal purple or non-purple lines generally segregated 1:1 for very dark purple to normal purple. F2 populations from very dark purple F1 plants generally segregated 3:1 for very dark purple to normal purple.

F1 plants of crosses made with plants homozygous for very dark purple are all similarly very dark purple. F2 populations of these crosses also segregate 3:1 very dark to normal purple.

The very dark purple trait is easily retained through up to eight generations if pedigree selection in different genetic backgrounds to obtain inbred lines and up to five generations of backcrossing to obtain counterpart male sterile seed parents.

Example 2

Development of Seed Parent Maintainer Line PA14B and Counterpart Male Sterile Seed, Parent Line PA14A$_4$ PA14B has a pedigree of: [45B×(63B×53-1)]-1-3-3-2-3-2-1-6.

45B, a dwarf purple sister line of NM9B was crossed with a very dark purple plant from the F$_1$ of (63B×53-1). Seed parent maintainer line 63B has pale purple virescent foliage (homozygous for a single recessive gene causing a non-lethal chlorophyll deficiency). A virescent PP3 plant was selected in the F$_2$ generation, and pedigree selection continued for six further generations to obtain PA14B.

The F2 selection was crossed to a CMS male sterile (51A$_4$×53-1) A$_4$. Five backcrosses to produce PA14A$_4$ male sterile seed parent were made concurrently with the selection process leading to PA14B, using pollen from each successive selection to pollinate phenotypically similar male sterile plants grown from the prior backcross.

PA14B and PA14A$_4$ are medium late flowering, dwarf (80 cm) PP3 plants with virescent foliage with delayed purple development, wide leaves and excellent head exertion Example 3

Development of Seed Parent Maintainer Line PA23B and Counterpart Male Sterile Seed, Parent Line PA23A$_4$ PA23B has a pedigree of: [45B×(63B×53-1)]-1-5-3-3-2-5-1-2.

45B, a dwarf purple sister line of NM9B was crossed with a very dark purple plant from the F$_1$ of (63B×53-1). Seed parent maintainer line 63B has pale purple virescent foliage (homozygous for a single recessive gene causing a chlorophyll deficiency). A virescent PP3 plant was selected in the F$_4$ generation, and pedigree selection continued for four further generations to obtain PA23B.

The F4 selection was crossed to a CMS male sterile from the first backcross from (51A$_4$×53-1) A$_4$ in the generation of PA$_1$4B. Four backcrosses to produce PA 23A$_4$ male sterile seed parent were then made concurrently with the selection process leading to PA23B, using pollen from each successive selection to pollinate phenotypically similar male sterile plants grown from the prior backcross.

PA 23B and PA23A$_4$ are very late flowering medium tall (110 cm) PP3 plants with virescent foliage with delayed purple development and wide leaves Example 4

Development of Seed Parent Maintainer Line PA40B and Counterpart Male Sterile Seed, Parent Line PA40A$_4$ PA40B has a pedigree of: [45B×(63B×53-1)]-1-5-3-2-3-1-1-6.

45B, a dwarf purple sister line of NM9B was crossed with a dark purple plant from the F$_1$ of (63B×53-1). Seed parent maintainer line 63B has pale purple virescent foliage (homozygous for a single recessive gene causing a chlorophyll deficiency). A dark purple PP3 plant was selected in the F$_4$ generation, and pedigree selection continued within all dark purple families for four further generations to obtain PA40B.

The F4 selection was crossed to CMS male sterile from the first backcross from (51A$_4$×53-1) A$_4$ in the generation of PA14A$_4$. Four backcrosses to produce PA40A$_4$ male sterile seed parent were then made concurrently with the selection process leading to PA40B, using pollen from each successive selection to pollinate phenotypically similar male sterile plants grown from the prior backcross.

PA40B and PA40A$_4$ plants are of medium maturity, dwarf (90 cm), with very dark purple foliage and wide leaves.

Example 5

Development of Seed Parent Maintainer Line PA57B and Counterpart Male Sterile Seed, Parent Line PA57A$_5$ PA57B has a pedigree of: [45B×(63B×53-1)]-1-6-5-4-3-2-2-3.

45B, a dwarf purple sister line of NM9B was crossed with a very dark purple plant from the F$_1$ of (63B×53-1). Seed parent maintainer line 63B has pale purple virescent foliage (homozygous for a single recessive gene causing a chlorophyll deficiency). Pedigree selection from a virescent PP3 plant in the F$_3$ generation was continued for five further generations to obtain PA57B.

PA57A$_5$ male sterile seed parent was generated by crossing the F3 selection to a male sterile plant from the cross of (81A$_5$×83)A$_5$ which was homozygous for the virescent gene. Five backcrosses to produce PA57A$_5$ male sterile seed parent were then made concurrently with the selection process leading to PA57B, using pollen from each successive selection to pollinate phenotypically similar male sterile plants grown from the prior backcross.

PA57B and PA57A$_5$ are late flowering medium tall (85 cm) PP3 plants with virescent foliage with delayed purple development, wide leaves and good head exertion.

Example 6

Development of Seed Parent Maintainer Line PA70B and Counterpart Male Sterile Seed, Parent Line PA70A$_5$, PA70B is Also a Restorer Line, PA70A$_4$R$_4$, in A$_4$ CMS PA70B has a pedigree of: [NM8A$_4$R$_4$×(NM8A$_4$R$_4$×53-1)]-2-1-2-1-1-4-1.

NM8A$_4$R$_4$, the male fertility restorer male parent of Purple Majesty, contains A$_4$ sterile cytoplasm but is also homozygous for a dominant R$_4$ nuclear gene. NM8A$_4$R$_4$ was used as the female parent in the backcross so ensuring that all progeny would contain the A$_4$ sterile cytoplasm. In the F4 generation of pedigree selection a plant was found that proved homozygous for R$_4$. PA70B resulted from three further generations of selection.

PA70A$_5$ male sterile seed parent was generated by crossing an F1 plant from the [NM8A$_4$R$_4$×(NM8A$_4$R$_4$×53-1)] backcross to a male sterile PP3 plant from the cross of (81A$_5$×83) A$_5$. Five backcrosses to produce PA70A$_5$ male sterile seed parent were then made concurrently with the selection process leading to PA70B, using pollen from each successive selection to pollinate phenotypically similar male sterile plants grown from the prior backcross.

PA70B(=PA70A$_4$R$_4$) and PA70A$_5$ are very early flowering dwarf (75 cm), PP3 plants with very dark purple foliage, and heads densely covered in 2 cm long purple bristles.

Example 7

Development of Seed Parent Maintainer Line PA81B and Counterpart Male Sterile Seed Parent Line PA81A$_4$ PA81B has a pedigree of: (92B×53-1)]-1-1-4-1-1-4-1-2.

92B, (line 02C77092) a late maturing dwarf purple line homozygous for the monogenic recessive trichomeless (tr) trait, was crossed with 53-1. Trichomeless plants have no hairs and a thicker shiny surface cuticle. A dark purple PP3 trichomeless plant was selected in the F$_2$ generation, and pedigree selection continued for seven further generations to obtain PA81B.

An F3 selection from the F2 trichomeless plant was crossed to trichomeless CMS male sterile (95A$_4$trx92tr) A$_4$. Five backcrosses to produce PA81A$_4$ male sterile seed parent were then made concurrently with the selection process leading to PA81B, using pollen from each successive selection to pollinate phenotypically similar male sterile plants grown from the prior backcross.

PA81B and PA81A$_4$ plants are dwarf (90 cm.) very late maturing, with very dark foliage and wide smooth shiny leaves.

Example 8

Discovery and Test Crosses

Line 02C77053 was selected from the cross of NM9, a normal purple line with IP 18293, a late maturing characterized source of purple plant color with wide hairy leaves, from the Pearl Millet World Collection held at ICRISAT. NM9 was selected from a cross between two experimental F1's each of which had IP 18293 in their parentage.

In 2002 a late flowering plant, designated 53-1 was noted at head emergence, but before blooming in family row 02C77053, to be an "extremely dark purple plant". Row 02C77053 was one of 9 similar uniformly normal purple F$_8$ sister families, totaling ±220 plants, derived from the cross NM 9×IP18293. The purple coloring of plant 53-1 was observed to be distinctly different from all plants in these families.

Plant 53-1 was both selfed and pollen used to make ten test crosses, two of which were made to closely related normal purple sister lines and 8 to unrelated lines, 6 of which were normal purple and 2 non-purple.

The progeny of the self of 53-1 segregated into only two mature plant purple color classes, 33 plants were very dark purple and 15 the normal purple. A Chi$^2$ test showed this was not different from a 3:1 assumption.

Only two mature plant color classes, very dark purple and normal purple, occurred in all F1's. Class color counts shown in Table 2 were tested against a 1:1 hypothesis and then for whether there was heterogeneity in the F1 frequencies compared to the average expected frequency.

TABLE 2

Test crosses made with plant 02C77053-1 as male parent.
F1 mature plant color counts and Chi$^2$ values for a 1:1 hypotheses and heterogeneity test

| Cross Number | Female Parent (a) | PP3 F1 plant counts Count | PP3 F1 plant counts expected | PP F1 plant counts Count | PP F1 plant counts Expected | Chi$^2$ | DF | P |
| --- | --- | --- | --- | --- | --- | --- | --- | --- |
| 1 | 51 (b) | 32 | 30 | 28 | 30 | 0.27 | 1 | .75-.50 |
| 2 | 54 (b) | 16 | 17.5 | 19 | 17.5 | 0.26 | 1 | .75-.50 |
| 3 | 07 | 17 | 14 | 11 | 14 | 1.29 | 1 | .50-.25 |
| 4 | 13 | 28 | 28.5 | 29 | 28.5 | 0.02 | 1 | >.90 |
| 5 | 45 | 26 | 22 | 18 | 22 | 1.45 | 1 | .25-.10 |
| 6 | 63 | 17 | 17 | 17 | 17 | 0.00 | 1 | .90 |
| 7 | 92 | 25 | 23 | 21 | 23 | 0.35 | 1 | .75-.50 |

TABLE 2-continued

Test crosses made with plant 02C77053-1 as male parent.
F1 mature plant color counts and Chi² values for a 1:1 hypotheses and heterogeneity test

| Cross Number | Female Parent (a) | PP3 F1 plant counts Count | PP3 F1 plant counts expected | PP F1 plant counts Count | PP F1 plant counts Expected | Chi² | DF | P |
|---|---|---|---|---|---|---|---|---|
| 8 | 98 | 10 | 12 | 14 | 12 | 0.67 | 1 | .50-.25 |
| 9 | 81 | 10 | 8.5 | 7 | 8.5 | 0.54 | 1 | .50-.25 |
| 10 | 108 | 13 | — | 5 (c) | — | — | — | — |
| Total | | 181 | | 164 | | 4.85 | 9 | |
| Pooled | | 181 | 172.5 | 164 | 172.5 | 0.84 | 1 | .50-.25 |
| Heterogeneity | | | | | | 4.01 | 8 | .90-.75 |

(a) - 02C77 number. Females in crosses 1-8 normal purple, 9 and 10 not purple.
(b) - Females closely related to 02C77053-1.
(c) - Sample size insufficient for analysis, no further seed.

The Chi² values show that none of the nine F1's differed significantly from the 1:1 hypothesis and that the heterogeneity test was not significant.

These observations and plant color frequencies suggest:

a) The crosses (1 and 2) to sister lines suggest that Plant 53-1 was heterozygous for an allele that induces very dark purple plant color.
b) The color frequencies in the progeny of the self of 53-1 indicates that the factor causing very dark purple is monogenic and dominant to normal purple.
c) The proportion, and similarities of color intensity of the color segregation in the six crosses to other normal purple lines, also suggests that plant 53-1 was heterozygous at a single locus, and show that the new allele is dominant in effect compared to normal purple plant color in other backgrounds.
d) Both F1's of crosses nine and ten to non purple lines again segregated into two similar classes, very dark purple and normal purple plants. The presence of very dark purple plants supports the dominant concept for the new allele.
e) the lack of heterogeneity among any of the F1 class frequencies suggests that the new allele will probably function normally in different genetic back grounds which, together with its dominant effect indicate the allele may be easily used in breeding contrasting desirable very dark purple lines.

One selfed plant, 53-1-1, from the 53-1 selfed population gave progeny that were uniformly dark purple, and was therefore homozygous for this allele. Since the symbols P, P1 and P2 had previously been used by various authors in research into the genetics of color in pearl millet, the new gene was designated PP3.

Example 9

Crosses with Known Purple Color Stocks

There are many published articles on genetic effects of red or purple pigmentation on various parts of the pearl millet plant, with 14 gene symbols suggested. Of these, five apply to the whole plant, or purple foliage, with one research note (Yadav, 1976) on coleoptile color. Only Hanna and Burton (1992) describe development and intensity of color, but none describe similarity or difference between homozygous or heterozygous pigmented plants.

In addition to NM-9, the seed parent of Purple Majesty, four whole plant red or purple stocks were obtained (Table 3) including the strongest color stock from the World Collection Accession No. IP8166, for comparison and crossing with PP3 stocks.

TABLE 3

| | Reference or source | Gene Contained |
|---|---|---|
| 1. IP 18293 | Azhaguvel, et. al., 2003 | PP |
| 2. IP 8166 | World Collection ex ICRISAT 2002 | None given |
| 3. Tift 89-18 | Hanna and Burton, 1992 | Rp2 |
| 4. Tift 89-19 | Hanna and Burton, 1992 | Rp1 |
| 5. NM9B | UNL (ex. IP 18293) | 'Pm' (PP by descent) |

Crosses were made between PP3 source 53-1-1 to color sources Nos. 1-4 above and No. 5 was crossed with the original 53-1-1 plant. The color sources are characterized in FIGS. 4-16. Observations made on F1 and F2 generations (F1 only with No. 4×53-1-1) are shown in Table 4.

Color stocks 1-4 (table 3) were used as females in crosses with 53-1-1. Color stock No. 5 (NM9B) was earlier crossed with 53-1. Line Tift 23 DB (normal green) was also crossed with a PP3 derived line PA70B, homozygous for PP3.

TABLE 4

Segregation in F1 and F2 generations (except for cross with Tift 89-19) of crosses to color stocks, recorded as presence or absence of the PP3 seedling marker (SM) or mature plant (MP) color type (PP3 or normal purple, (NP))

| Cross | Generation | SM | MP | PP3 | NP | Green |
|---|---|---|---|---|---|---|
| IP18293 × 53-1-1 | F1 | | + | 7 | 0 | 0 |
| | F2 | + | | 83 | 37 (a) | 0555 |
| IP8166 × 53-1-1 | F1 | | + | ±20 | (1)* | 0 |
| | F2 | + | | 56 | 16 (b) | 0 |
| Tift89-18 × 53-1-1 | F1 | | + | 5 | 0 | 0 |
| | F2 | + | | 85 | 26 (c) | 0 |
| Tift89-19 × 53-1-1 | F1 | + | | 56 | (4)* | 0 |
| | (F2 N/A) | | | | | |
| NM9B × 53-1 | F1 | | + | 17 | 11** | 0 |
| | F2 | + | | 24 | 9 (d) | 0 |
| Tift23Db × PA70B | F1 | | + | ±20 | 0 | 0 |
| | F2 (#1) | + | | 90 | 0 | 31 (e) |
| | F2 (#2) | + | | 89 | 0 | 30 (f) |

*female parent selfs
**see cross 3, Table 2
Chi² values for 3:1 assumption in F2's.
(a) 2.178 (P = 0.25-0.10)
(b) 0.296 (P = 0.75-0.50)
(c) 0.099 (P = 0.90-0.75)
(d) 0.108 (P = 0.75-0.50)
(e) 0.023 (P = 0.90-0.75)
(f) 0.026 (P = 0.90-0.75)

The F1 populations show that the phenotypic effects of the PP3 allele are dominant to the purple genes in all color stock parents. In each of the F2 populations assessed, PP3 segregates as a simple gene dominant to other purple or red colors, fitting a 3:1 ratio.

The F1 plants were all PP3 in the cross between normal green line Tift 23 DB and the PP3 derived line, PA 70B. Two F2 samples were separately grown from the same F1 plant. The first sample was scored for the presence or absence of the PP3 seedling marker, the second sample was scored for the absence or presence and type of mature plant purple coloration. Both samples segregated into two classes. In the seedling test, those without the first leaf marker were grown on to the three leaf stage when the presence of any purple type can be determined. All were without any purple and therefore were classified as green. In the sample grown to maturity, all purple plants were very dark purple PP3 plants and none were normal purple, the remainder were normal green. The results from each of these two F2 populations were in close agreement with a 3:1 ratio.

Summary of Expression Effects:

The daily development of red/purple pigmentation in all the other sources of pigmentation in pearl millet is light induced. Hence the emerging bases of new leaves, and the part of the head emerged from leaf sheath during the previous night are green at dawn until mid-morning. However in PP3 plants, leaves and heads already show pigment development prior to exposure to daylight. This is also manifested in the coloration by anthesis of the underside of leaves and the peduncle and the parts of internodes covered by leaf sheaths. At anthesis these covered parts in PP3 plants are strongly pigmented, in the other pigmented stocks these are either normal green or very slightly pigmented.

Color on First Leaf

All red/purple sources produced some color on margins and upper surface of first leaf, (and on margins and under side of midrib on second and subsequent leaves). Yadav (1976) does not describe the distribution of color on the coleoptile. Other color sources, particularly red (Rp1) and purple (Rp2) from Hanna and Burton (1992) produced color on midrib keels on subsequent leaves, but not on the midrib keel of the first leaf before 10 days old. By this time PP3 produces a distinct thin dark purple line on the midrib keel on the underside of the first leaf extending down the leaf sheath. The early presence of this purple line under the first leaf therefore provides a definitive seedling marker for PP3. This purple line is expressed on all chlorophyll variations (normal, virescent or albino).

Purple pigmentation within the stem in PP3 plants begins to develop before head emergence, and reaches maximum at grain filling. Pigmentation is strongest in the interior of the lower internodes (see FIG. 22), but it is also evident in the vascular bundles in the peduncles at grain maturity. The interior of stems in all other sources of purple plant color in pearl millet at plant maturity are pale yellow/greenish, or pale brownish, occasionally with small light purple areas localized at the edges of the nodes.

Strength of Color

In all sources of color, including PP3, pigmentation on all organs strengthens with age and further exposure to daylight. However, in crosses between PP3 and the other purple color sources at or before heading, the purple color development is always more intense and darker in PP3 plants, than other purple, but non PP3 plants in same F2 families. The dominance and clear effect of PP3 in crosses with all other color sources is strong. The color in heterozygous PP3 pp 3 seedlings and plants closely resembles that of PP3 PP3 plants. This is unlike the purple source used in Purple Majesty (believed to be the PP gene by descent but can conveniently be called Pm) which is semi-dominant and subject to background modification. Pm×normal green gives a pale purple F1 hybrid. Pm is thus needed in both parents to obtain a sufficiently purple hybrid. However, the purple coloration of Purple Majesty (Pm Pm) at flowering is not as intense as a PP3 pp 3 or PP3×Pm hybrid. F2s of Pm×pm (normal green) crosses do not clearly segregate into purple/green classes, but exhibit a range of purple intensities. The PP3 segregates in the F2's of crosses with PP3×other color stocks do not show an intermediate color range.

A recessive virescent gene, which causes a large but non lethal reduction in total chlorophyll content with a relatively higher reduction in chlorophyll part a than b, making leaves yellow green, also delays and reduces the development of purple pigmentation in leaves, whether due to PP or PP3. The difference in effects of the two in leaf whorl coloration, and the relative intensity of upper and lower leaf surface coloration exist as before, but at muted levels. The strength of the coloration on the lower midrib on the first leaf of virescent PP3 seedlings is not diminished (see FIG. 19) nor is the development of purple pigment in the interior of stems of mature virescent PP3 plants.

The PP3 gene therefore affects different organs at different times as they develop in the plant, enabling the presence of the PP3 alleles to be identified at the seedling stage, and at any time from full leaf coloration to plant maturity.

Figure 23:
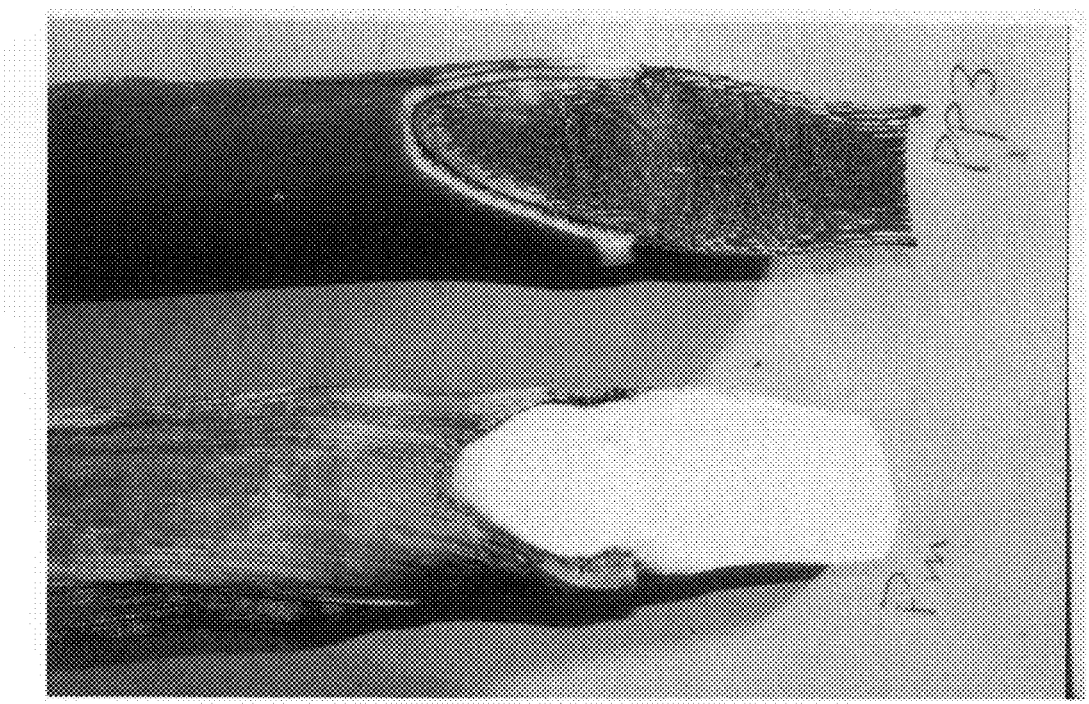

Elephant grass (*Pennisetum purpureum*) (EG) despite its name is green and shows no adult lamina or stem pigmentation under normal conditions. Crosses of Pm×EG show faint purple leaf coloration at ±8 weeks gradually increasing to pale purple and exposed stem surfaces also become pale purple at 16-20 weeks. At this time the interior (pith) of basal stems is green (not purple) when cut (FIG. 23). However, leaves and stems of PP3×EG crosses are strongly purple at ±8 weeks onwards. Exposed stem surfaces go black purple later, and when cut near base, contain a deep purple/black interior (FIG. 23).

PP3 distinctly intensifies and deepens purple color on all plant parts, increasing horticultural appeal. Interspecific hybrids with *Pennisetum purpureum* (elephant grass), with previous purple genes are weakly purple, with PP3 they are strongly purple. Such interspecific hybrids are perennial and are propagated by cuttings an economically attractive process for the horticulture industry.

New Gene for Purple Plant Color in Pearl Millet (Designated PP3).

Compared to existing red/purple types of pearl millet this new gene distinctly intensifies the purple pigmentation that develops in leaf, stem and heads. The phenotypic effect of PP3 in either the homozygous or heterozygous state can readily be distinguished in the presence or absence of all other colors at the seedling, at leaf coloration, heading and mature plant stages.

Deposits

Applicant will make a deposit of at least 2500 seeds of Pearl Millet Variety 53-1-1 with the American Type Culture Collection (ATCC), Manassas, Va. 20110 USA, ATCC Deposit No. PTA-9648. The seeds deposited with the ATCC on Dec. 8, 2008 will be taken from the deposit maintained by University of Nebraska-Lincoln 105C KCR Department of Agronomy & Horticulture Lincoln, Neb. 68588-0467 since prior to the filing date of this application. Access to this deposit will be available during the pendency of the application to the Commissioner of Patents and Trademarks and persons determined by the Commissioner to be entitled thereto upon request. Upon issue of claims, Applicant will make available to the public, pursuant to 37 CFR 1.808, a deposit of at least 2500 seeds of variety 53-1-1 with the American type Culture Collection (ATCC), 10801 University Boulevard, Manassas, Va. 20110-2209. This deposit of the Pearl Millet Variety 53-1-1 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§1.801-1.809, including providing an indication of the viability of the sample. Applicant has no authority to waive any restrictions imposed by law on the transfer of biological material or its transportation in commerce. Applicant does not waive any infringement of his rights granted under this patent or under the Plant Variety Protection Act (7 USC 2321 et seq.).

REFERENCES

Anand, Kumar, K. and Andrews, D. J. 1993. Genetics of qualitative traits in pearl millet: a review. *Crop Sci.* 33:1-20.

Azhaguvel, P., C. T. Hash, P. Rangaswamy and A. Sharma. 2003. Mapping the d, and d2 dwarfing genes and the Purple Color Locus P in pearl millet. *J. Hered.* 94(2):155-159.

Gill, B. S. 1969. Inheritance of pigmentation in some plant parts of pearl millet. *Indian J. Genet. Plant Breed.* 29:468-472.

Hanna, W. W. and Burton, G. W. 1992. Genetics of red and purple color in pearl millet. *J. Hered.* 83:386-388.

Royal Horticultural Society. 1995. Colour Charts. London SW1 2PE UK.

Yadav, R. P. 1976. A note on inheritance of purple pigmentation in the coleoptilar leaf of pearl millet (Pennisetum typhoides, S+H). *Curr. Sci.* 45:197.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant variety and the like may be practiced within the scope of the invention, as limited only by the scope of the appended claims.

What is claimed is:

1. A method of introducing a desired trait into millet variety 53-1-1 comprising:
   (a) crossing 53-1-1 plants grown from 53-1-1 seed, representative seed of which has been deposited under ATCC Accession No. PTA-648, with plants of another millet line that comprise a desired trait to produce progeny plants;
   (b) selecting progeny plants that have the desired trait to produce selected progeny plants;
   (c) crossing the selected progeny plants with the 53-1-1 plants to produce backcross progeny plants;
   (d) selecting for backcross progeny plants that have the desired trait to produce selected backcross progeny plants; and
   (e) repeating steps (c) and (d) three or more times in succession to produce selected fourth or higher backcross progeny plants that comprise the desired trait and the remaining morphological and physiological characteristics of millet variety 53-1-1.

2. A seed produced by the process of claim 1.

3. A plant produced by the process of claim 1.

4. A pearl millet seed of variety 53-1-1 as deposited under ATCC Accession No. PTA-9648.

5. A plant or plant part or progeny of the pearl millet variety produced by the process of claim 1, wherein the plant or plant part or progeny comprises the desired trait and the remaining morphological and physiological characteristics of millet variety 53-1-1.

* * * * *

UNITED STATES PATENT AND TRADEMARK OFFICE
CERTIFICATE OF CORRECTION

PATENT NO. : 7,750,214 B2  Page 1 of 1
APPLICATION NO. : 12/011049
DATED : July 6, 2010
INVENTOR(S) : David John Andrews It is certified that error appears in the above-identified patent and that said Letters Patent is hereby corrected as shown below:

Column 22, Claim 1, line 16
After Accession No. delete "PTA-648"
After Accession No. add --PTA-9648--

Signed and Sealed this

Seventeenth Day of August, 2010

David J. Kappos
*Director of the United States Patent and Trademark Office*